(12) United States Patent
Agrawal et al.

(10) Patent No.: US 10,569,072 B2
(45) Date of Patent: Feb. 25, 2020

(54) HEMOSTASIS VALVES AND METHODS FOR MAKING AND USING HEMOSTASIS VALVES

(71) Applicant: BOSTON SCIENTIFIC LIMITED, Hamilton (BM)

(72) Inventors: Sumit Agrawal, Haryana (IN); Henry J. Pepin, Loretto, MN (US)

(73) Assignee: BOSTON SCIENTIFIC LIMITED, Hamilton (BM)

( * ) Notice: Subject to any disclaimer, the term of this patent is extended or adjusted under 35 U.S.C. 154(b) by 185 days.

(21) Appl. No.: 15/904,829

(22) Filed: Feb. 26, 2018

(65) Prior Publication Data
US 2018/0256872 A1    Sep. 13, 2018

Related U.S. Application Data

(60) Provisional application No. 62/470,677, filed on Mar. 13, 2017.

(51) Int. Cl.
*A61M 39/06*    (2006.01)

(52) U.S. Cl.
CPC ........ *A61M 39/06* (2013.01); *A61M 39/0613* (2013.01); *A61M 2039/062* (2013.01); *A61M 2039/0673* (2013.01)

(58) Field of Classification Search
CPC .... A61M 2039/062; A61M 2039/0673; A61M 39/06; A61M 39/0613; A61M 2039/0633;
(Continued)

(56) References Cited

U.S. PATENT DOCUMENTS

| 3,180,334 A | 4/1965 | Glenn |
| 4,000,739 A | 1/1977 | Stevens |

(Continued)

FOREIGN PATENT DOCUMENTS

| WO | 9813083 A1 | 4/1998 |
| WO | 0062844 A1 | 10/2000 |

(Continued)

OTHER PUBLICATIONS

International Search Report and Written Opinion for Application No. PCT/US2018/019674, 13 pages, dated Jun. 13, 2018.

*Primary Examiner* — Brandy S Lee
(74) *Attorney, Agent, or Firm* — Seager, Tufte & Wickhem LLP

(57) ABSTRACT

Hemostasis valves and methods for making and using hemostasis valves are disclosed. An example hemostasis valve may include a main body having a proximal end region. A cartridge may be at least partially disposed within the proximal end region. The cartridge may include a seal member. The seal member may be designed to shift between an open configuration and a sealed configuration. A plunger, having an inner tubular region and a distal end, may be coupled to the proximal end region of the main body. The distal end of the inner tubular region may be spaced a clearance distance from a proximal end of the seal member so that when the seal member is in the sealed configuration and exposed to pressures of 80-250 pounds per square inch, the seal member deflects into contact with the distal end of the inner tubular region and remains in the sealed configuration.

20 Claims, 8 Drawing Sheets

(58) Field of Classification Search
CPC .... A61M 2039/064; A61M 2039/0653; A61M 2039/0686; A61M 39/0606; A61M 39/26; A61M 2039/066; A61M 2039/1077; A61M 2039/267; A61M 25/0097; A61M 39/045; A61M 39/0693; A61M 39/10; A61M 39/286

See application file for complete search history.

(56) References Cited

U.S. PATENT DOCUMENTS

| | | | |
|---|---|---|---|
| 4,177,814 A | 12/1979 | Knepshield et al. | |
| 4,240,411 A | 12/1980 | Hosono | |
| 4,424,833 A | 1/1984 | Spector et al. | |
| 4,430,081 A | 2/1984 | Timmermans | |
| 4,726,374 A * | 2/1988 | Bales | A61M 39/0613 277/510 |
| 5,330,435 A * | 7/1994 | Vaillancourt | A61M 39/045 241/149 |
| 5,489,274 A * | 2/1996 | Chu | A61M 39/0613 604/167.05 |
| 5,591,137 A | 1/1997 | Stevens | |
| 2004/0210194 A1 | 10/2004 | Bonnette et al. | |
| 2013/0197621 A1* | 8/2013 | Ryan | A61B 17/0057 623/1.11 |

FOREIGN PATENT DOCUMENTS

| | | |
|---|---|---|
| WO | 0117587 A1 | 3/2001 |
| WO | 2005018732 A1 | 3/2005 |

\* cited by examiner

HEMOSTASIS VALVES AND METHODS FOR MAKING AND USING HEMOSTASIS VALVES

CROSS REFERENCE TO RELATED APPLICATIONS

This application claims the benefit of U.S. Provisional Patent Application Ser. No. 62/470,677 filed on Mar. 13, 2017, the disclosure of which is incorporated herein by reference.

TECHNICAL FIELD

The present disclosure pertains to medical devices, and methods for manufacturing medical devices. More particularly, the present disclosure pertains to hemostasis valves and methods for making and using hemostasis valves

BACKGROUND

A wide variety of medical devices have been developed for medical use, for example, intravascular use. Some of these devices include guidewires, catheters, and the like. These devices are manufactured by any one of a variety of different manufacturing methods and may be used according to any one of a variety of methods. Of the known medical devices and methods, each has certain advantages and disadvantages. There is an ongoing need to provide alternative medical devices as well as alternative methods for manufacturing and using medical devices.

BRIEF SUMMARY

This disclosure provides design, material, manufacturing method, and use alternatives for medical devices. An example hemostasis valve is disclosed. The hemostasis valve comprises: a main body having a proximal end region; a cartridge at least partially disposed within the proximal end region, the cartridge including a seal member; wherein the seal member is designed to shift between an open configuration and a sealed configuration; a plunger coupled to the proximal end region of the main body, the plunger having an inner tubular region having a distal end; wherein the distal end of the inner tubular region is spaced a clearance distance from a proximal end of the seal member so that when the seal member is in the sealed configuration and exposed to pressures of 80-250 pounds per square inch, the seal member deflects into contact with the distal end of the inner tubular region and remains in the sealed configuration.

Alternatively or additionally to any of the embodiments above, the clearance distance has an axial dimension of 0.1 to 5 millimeters.

Alternatively or additionally to any of the embodiments above, the clearance distance has an axial dimension of 0.3 to 2 millimeters.

Alternatively or additionally to any of the embodiments above, the clearance distance is designed so that when the seal member is in the sealed configuration and exposed to pressures of 100-250 pounds per square inch, the seal member deflects into contact with the distal end of the inner tubular region and remains in the sealed configuration.

Alternatively or additionally to any of the embodiments above, the clearance distance is designed so that when the seal member is in the sealed configuration and exposed to pressures of 80-200 pounds per square inch, the seal member deflects into contact with the distal end of the inner tubular region and remains in the sealed configuration.

Alternatively or additionally to any of the embodiments above, the proximal end region of the main body includes a retaining protrusion.

Alternatively or additionally to any of the embodiments above, the plunger has a distal retaining flange designed to engage the retaining protrusion.

Alternatively or additionally to any of the embodiments above, a spring member is disposed within the plunger and engaged with a proximal end of the plunger.

Alternatively or additionally to any of the embodiments above, further comprising a nut threadably engaged with one or more threads along the proximal end region of the main body.

Alternatively or additionally to any of the embodiments above, the inner tubular region has a wall thickness that varies along the length thereof.

Alternatively or additionally to any of the embodiments above, the inner tubular region has an inner diameter that varies along the length thereof.

A hemostasis valve is disclosed. The hemostasis valve comprises: a main body having a proximal end region; a cartridge at least partially disposed within the proximal end region, the cartridge including a seal member; wherein the seal member is designed to shift between an open configuration and a sealed configuration; a plunger coupled to the proximal end region of the main body, the plunger having an inner tubular region having a distal end; wherein the seal member and the plunger are arranged so that there is a clearance distance between a proximal face of the seal member and the distal end of the inner tubular region such that when the seal member is in the sealed configuration and exposed to pressures of 80-250 pounds per square inch, the proximal face of the seal member deflects into contact with the distal end of the inner tubular region and remains in the sealed configuration.

Alternatively or additionally to any of the embodiments above, the clearance distance has an axial dimension of 0.1 to 5 millimeters.

Alternatively or additionally to any of the embodiments above, the clearance distance has an axial dimension of 0.3 to 2 millimeters.

Alternatively or additionally to any of the embodiments above, the clearance distance is designed so that when the seal member is in the sealed configuration and exposed to pressures of 100-250 pounds per square inch, the seal member deflects into contact with the distal end of the inner tubular region and remains in the sealed configuration.

Alternatively or additionally to any of the embodiments above, the clearance distance is designed so that when the seal member is in the sealed configuration and exposed to pressures of 80-200 pounds per square inch, the seal member deflects into contact with the distal end of the inner tubular region and remains in the sealed configuration.

Alternatively or additionally to any of the embodiments above, the proximal end region of the main body includes a retaining protrusion and wherein the plunger has a distal retaining flange designed to engage the retaining protrusion.

Alternatively or additionally to any of the embodiments above, further comprising a nut threadably engaged with one or more threads along the proximal end region of the main body.

A hemostasis valve is disclosed. The hemostasis valve comprises: a main body having a threaded proximal end region; a nut threadably engaged with the threaded proximal end region; a cartridge at least partially disposed within the threaded proximal end region, the cartridge including a seal member; wherein the seal member is designed to shift between an open configuration and a sealed configuration; a plunger coupled to the threaded proximal end region of the main body, the plunger having an inner tubular region having a distal end; wherein the seal member and the plunger are arranged so that there is a clearance distance between a proximal face of the seal member and the distal end of the inner tubular region such that when the seal member is in the sealed configuration and exposed to pressures of 80-250 pounds per square inch, the proximal face of the seal member deflects into contact with the distal end of the inner tubular region and remains in the sealed configuration.

Alternatively or additionally to any of the embodiments above, the clearance distance has an axial dimension of 0.3 to 2 millimeters and wherein the clearance distance is designed so that when the seal member is in the sealed configuration and exposed to pressures of 80-200 pounds per square inch, the seal member deflects into contact with the distal end of the inner tubular region and remains in the sealed configuration.

The above summary of some embodiments is not intended to describe each disclosed embodiment or every implementation of the present disclosure. The Figures, and Detailed Description, which follow, more particularly exemplify these embodiments.

BRIEF DESCRIPTION OF THE DRAWINGS

The disclosure may be more completely understood in consideration of the following detailed description in connection with the accompanying drawings, in which.

Figure 1:
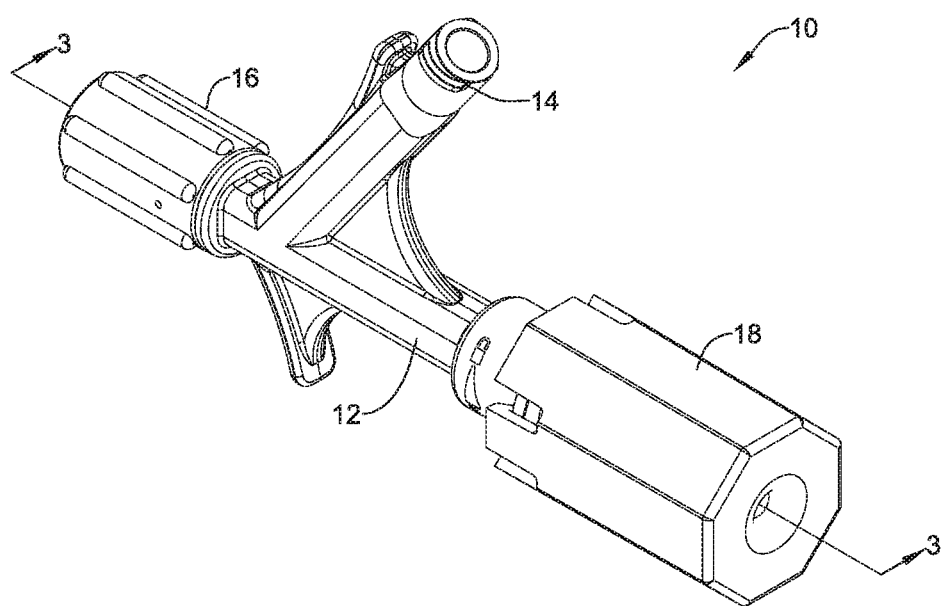
FIG. 1 is a perspective view of an example hemostasis valve.

While the disclosure is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the spirit and scope of the disclosure.

DETAILED DESCRIPTION

For the following defined terms, these definitions shall be applied, unless a different definition is given in the claims or elsewhere in this specification.

All numeric values are herein assumed to be modified by the term "about", whether or not explicitly indicated. The term "about" generally refers to a range of numbers that one of skill in the art would consider equivalent to the recited value (e.g., having the same function or result). In many instances, the terms "about" may include numbers that are rounded to the nearest significant figure.

The recitation of numerical ranges by endpoints includes all numbers within that range (e.g. 1 to 5 includes 1, 1.5, 2, 2.75, 3, 3.80, 4, and 5).

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

It is noted that references in the specification to "an embodiment", "some embodiments", "other embodiments", etc., indicate that the embodiment described may include one or more particular features, structures, and/or characteristics. However, such recitations do not necessarily mean that all embodiments include the particular features, structures, and/or characteristics. Additionally, when particular features, structures, and/or characteristics are described in connection with one embodiment, it should be understood that such features, structures, and/or characteristics may also be used connection with other embodiments whether or not explicitly described unless clearly stated to the contrary.

The following detailed description should be read with reference to the drawings in which similar elements in different drawings are numbered the same. The drawings, which are not necessarily to scale, depict illustrative embodiments and are not intended to limit the scope of the invention.

A number of medical procedures, for example intravascular procedures, utilize medical devices within body lumens. For example, some intravascular procedures include the placement of a guidewire, guide catheter, interventional device, or the like in a blood vessel. Because fluid under pressure (e.g., blood) is present within the blood vessel, fluid could travel along or through the medical device and escape or leak from the patient. In some instances, it may be desirable to dispose a hemostasis valve or hemostasis valve assembly at the proximal end of a medical device to reduce or otherwise limit the leaking of fluids/blood from the proximal end of the device.

An example hemostasis valve 10 is shown in FIG. 1. The hemostasis valve 10 may include a main body 12. The main body 12 may include a side port 14. The side port 14 may be connected to another device such as an infusion device, an inflation device, or the like. An adapter 16 may be coupled to the distal end of the main body 12. The adapter 16 may be used to couple the hemostasis valve 10 to a device such as a catheter. A plunger 18 may be coupled to the proximal end of the main body 12. The plunger 18 may be used to activate or otherwise close a seal (e.g., as discussed herein) within the hemostasis valve 10. These and other features of the hemostasis valve 10 are discussed herein.

Figure 2:
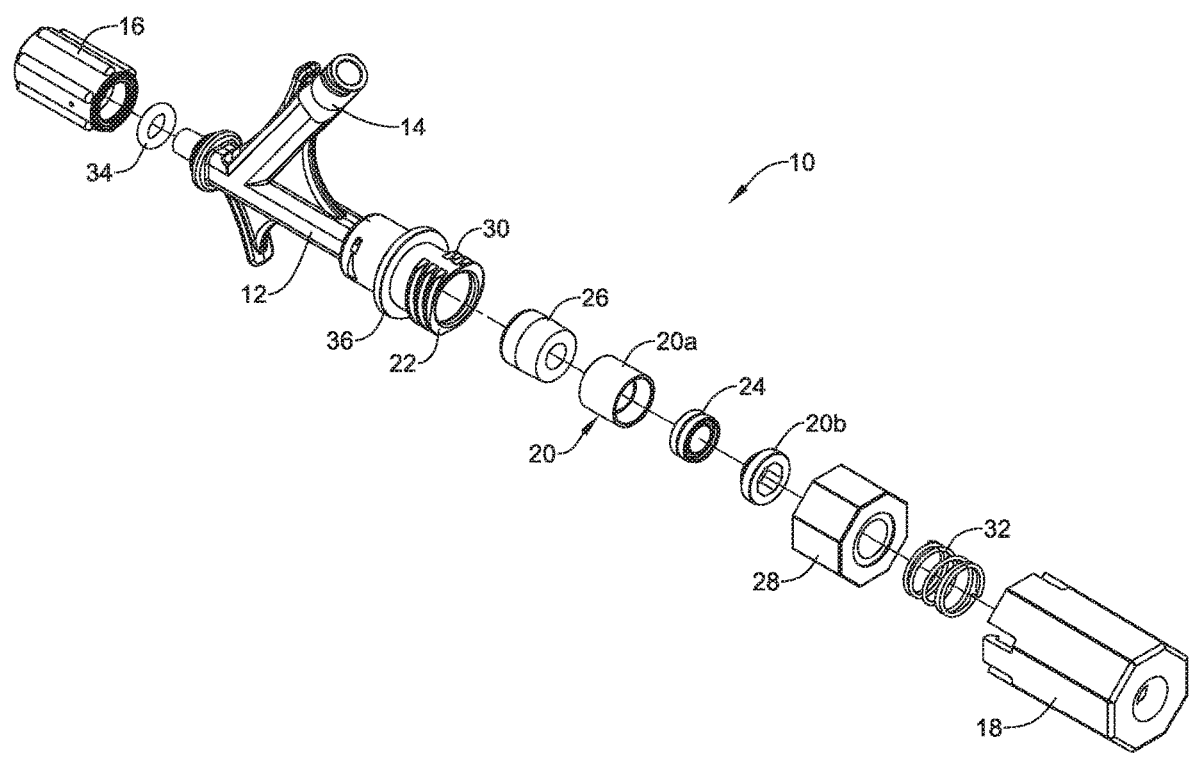
FIG. 2 is an exploded view of an example hemostasis valve.

FIG. 2 is an exploded view of the hemostasis valve 10. Here, the various components of the hemostasis valve 10 can be seen. For example, the hemostasis valve 10 may include a cartridge 20. The cartridge 20, which may include two pieces 20a, 20b that are coupled to one another (e.g., press fit, thermally bonded, adhesively bonded, etc.), may be arranged so that at least a portion thereof can be disposed within a proximal end region 22 of the main body 12. A first seal member 24 may be disposed within the cartridge 20. A second seal member 26 may be disposed within the proximal end region 22 of the main body 12. In at least some instances, the second seal member 26 may be disposed distally of the cartridge 20. The second seal member 26 may include a textured distal surface, grooves or wells formed therein, or the like. In addition or in the alternative, the second seal member 26 may include a proximal region with a reduced diameter. A nut 28 may be coupled to the proximal end region 22 of the main body 12, for example at one or more threads 30 formed along the proximal end region 22.

Other features of the hemostasis valve 10 that can be seen in FIG. 2 include a spring member 32 and an O-ring 34. The spring member 32 may be coupled to the plunger 18. In at least some instances, the spring member 32 may be designed to exert a proximally directed force on the plunger 18. The O-ring 34 may be positioned adjacent to the adapter 16. In addition, a ring member or "snap ring" 36 may be disposed along the proximal end region 22 of the main body 12.

Figure 3:
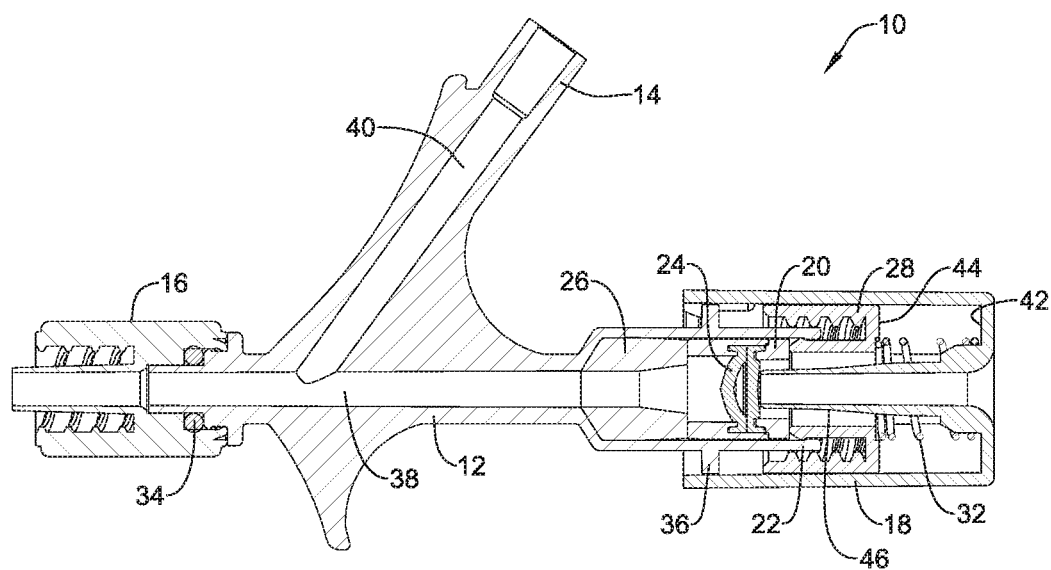
FIG. 3 is a cross-sectional view taken through line 3-3 in FIG. 1.

FIG. 3 is a cross-sectional view the hemostasis valve 10. Here some of the structural features of the hemostasis valve 10 can be seen. For example, the hemostasis valve 10 may include a central lumen 38. In general, the central lumen 38 is designed to be placed into fluid communication with one or more lumens of a device coupled to the adapter 16. A second or infusion lumen 40 may be defined adjacent to the side port 14. The second lumen 40 may be in fluid communication with the central lumen 38.

As indicated above, the hemostasis valve 10 is designed so that it may be coupled to another device. For example, the adapter 16, which may take the form of a Tuohy-Borst or other type of connector, may be engaged with the proximal end of the other device. When connected (and with the plunger 18 in the configuration shown in FIG. 3), the second seal member 26 may be in an open state or configuration. Conversely, the first seal member 24 may be in a closed or sealed configuration when the hemostasis valve 10 is connected to the other device (and with the plunger 18 in the configuration shown in FIG. 3).

Collectively, when the hemostasis valve 10 is connected to another device and in the configuration shown in FIG. 3, the hemostasis valve 10 is able to substantially hold a fluid-tight seal that substantially prevents the backflow and/or leakage of body fluids (e.g., blood). At some point during a medical intervention, it may be desirable to infuse additional fluids such as contrast media through the hemostasis valve 10. This may include attaching an infusion device to the side port 14. Because the first seal member 24 may be designed to substantially prevent the backflow and/or leakage of relatively-low pressure fluids, if the infusion device infuses fluids at a relatively high pressure, it is possible that the infusion fluid may be able to flow through the first seal member 24.

Figure 4:
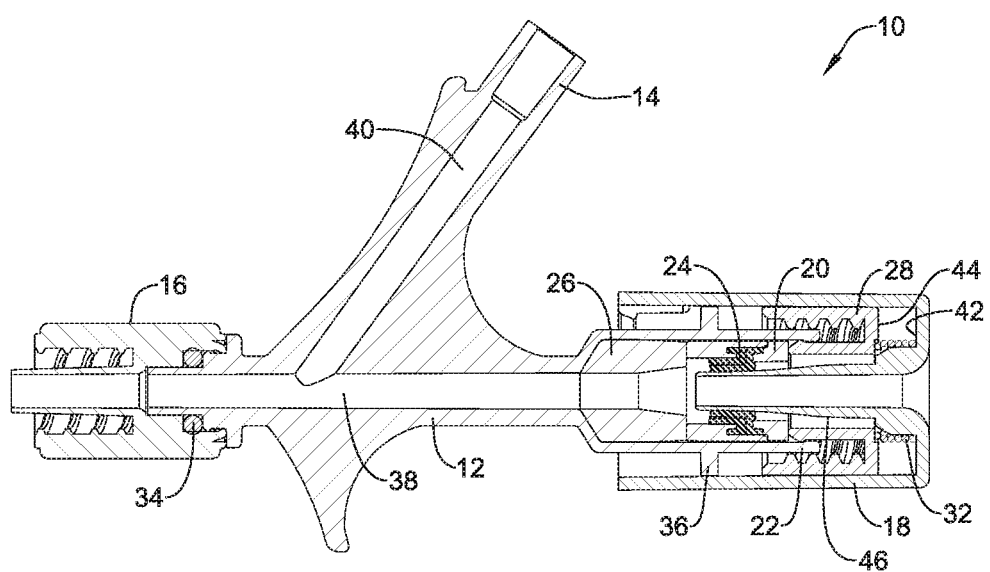
FIG. 4 is a cross-sectional view of an example hemostasis valve.
Figure 5A:
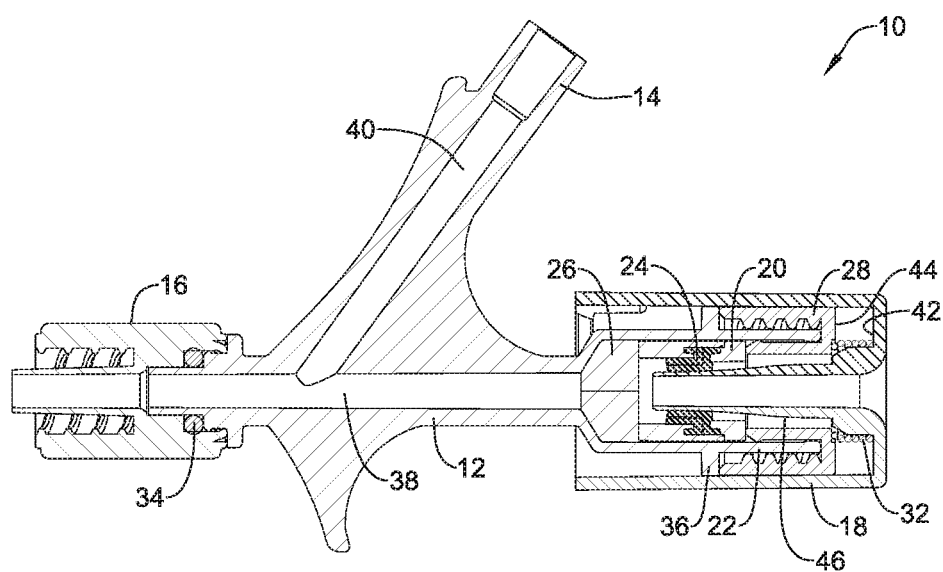
FIGS. 5A-5B is a cross-sectional view of an example hemostasis valve.

In order to prevent backflow of relatively high pressure fluids, the hemostasis valve 10 can be actuated to close or "seal" the second seal member 26. To do so, the plunger 18 may initially be urged distally until a distally-facing, proximal end surface or cap 42 of the plunger 18 is disposed adjacent to a proximal end region 44 of the nut 28 as shown in FIG. 4. When doing so, a tubular region 46 of the plunger 18 may extend through (and open) the first seal member 24. In addition, a portion of the plunger 18 may move distally beyond the ring member 36. With the cap 42 of the plunger 18 disposed adjacent to the nut 28, the plunger 18 can be rotated (e.g., in a clockwise direction) to close the second seal member 26 as shown in FIG. 5A. This rotation may cause the nut 28 to rotate and move distally. Because the distal end region of the nut 28 may be engaged with the cartridge 20, distal movement of the nut 28 urges the cartridge 20 distally within the proximal end region 22 of the main body 12 such that the cartridge 20 engages and deforms the second seal member 26, thereby shifting the second seal member 26 to the closed or sealed configuration.

Figure 5B:
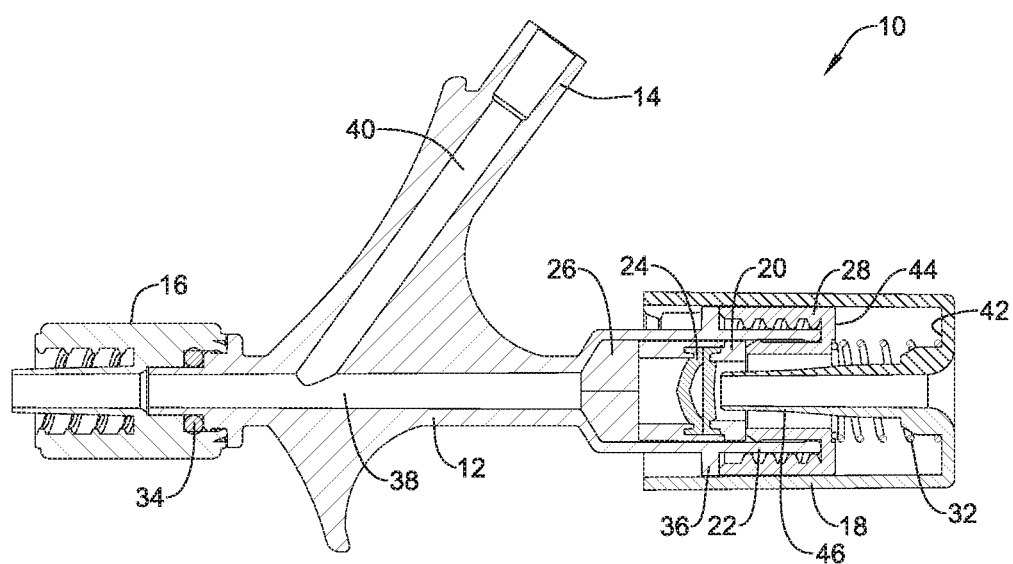

The plunger 18 may be released or otherwise allowed to move proximally, as shown in FIG. 5B, which may reclose the first seal member 24 (while the second seal member 26 remains closed).

As indicated above, the first seal member 24 may be described as a "low pressure" seal, designed to prevent the flow of fluids at a relatively low pressure. For example, the first seal member 24 may be designed to withstand pressures on the order of about 75-85 pounds per square inch (psi). While this performance is considered to be acceptable, it may desirable to further enhance the performance of the first seal member 24. Disclosed herein are hemostasis valves where the performance of the first seal member 24 is enhanced.

Figure 6:
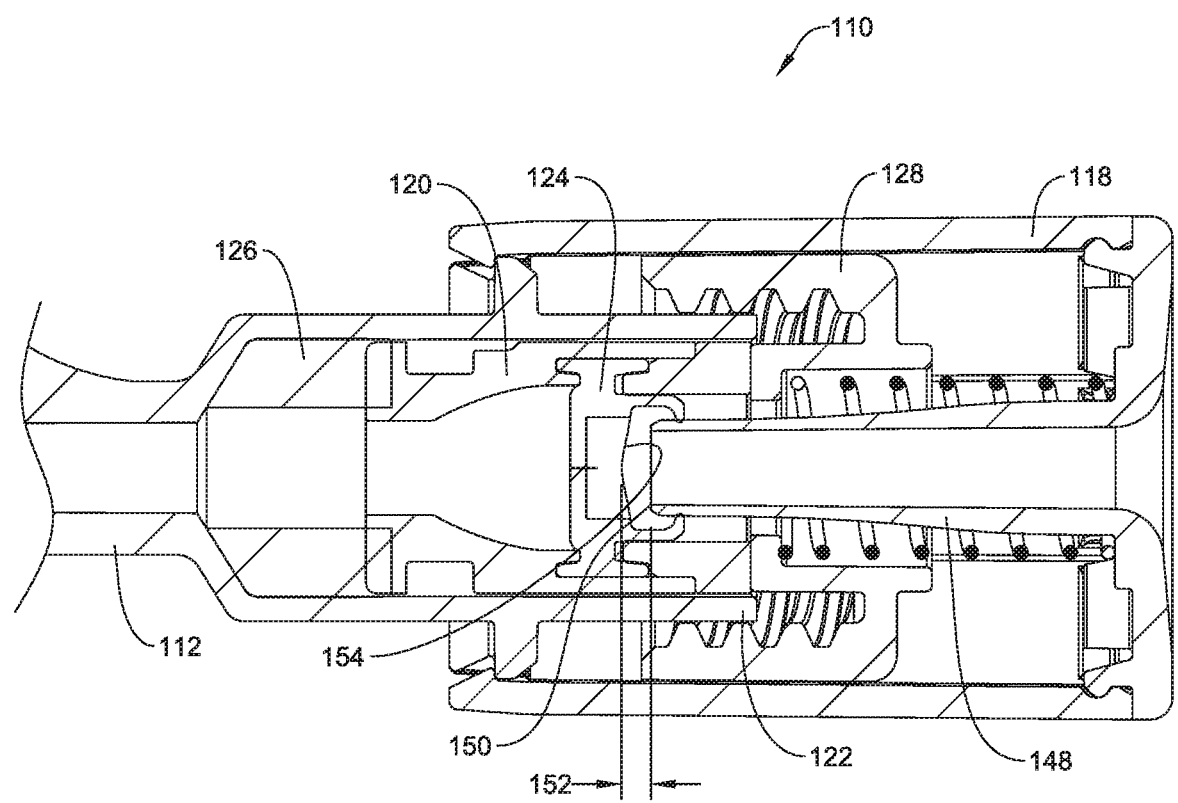
FIG. 6 is a cross-sectional view of a portion of an example hemostasis valve.

FIG. 6 illustrates a portion of another example hemostasis valve 110 that may be similar in form and function to other hemostasis valve disclosed herein. While only a portion of the hemostasis valve 110 is shown, it can be appreciated that the reminder of the hemostasis valve 110 may include structures similar to or the same as those in the hemostasis valve 10 described above. The hemostasis valve 110 includes a main body 112 having a proximal end region 122. A cartridge 120 may be disposed at least partially within the proximal end region 122. The cartridge 120 may include a first seal member 124. A second seal member 126 may also be at least partially disposed within the proximal end region 122. A plunger 118 may be coupled to the proximal end region 122 and a nut 128 may be threadably engaged with the proximal end region 122.

Figure 7:
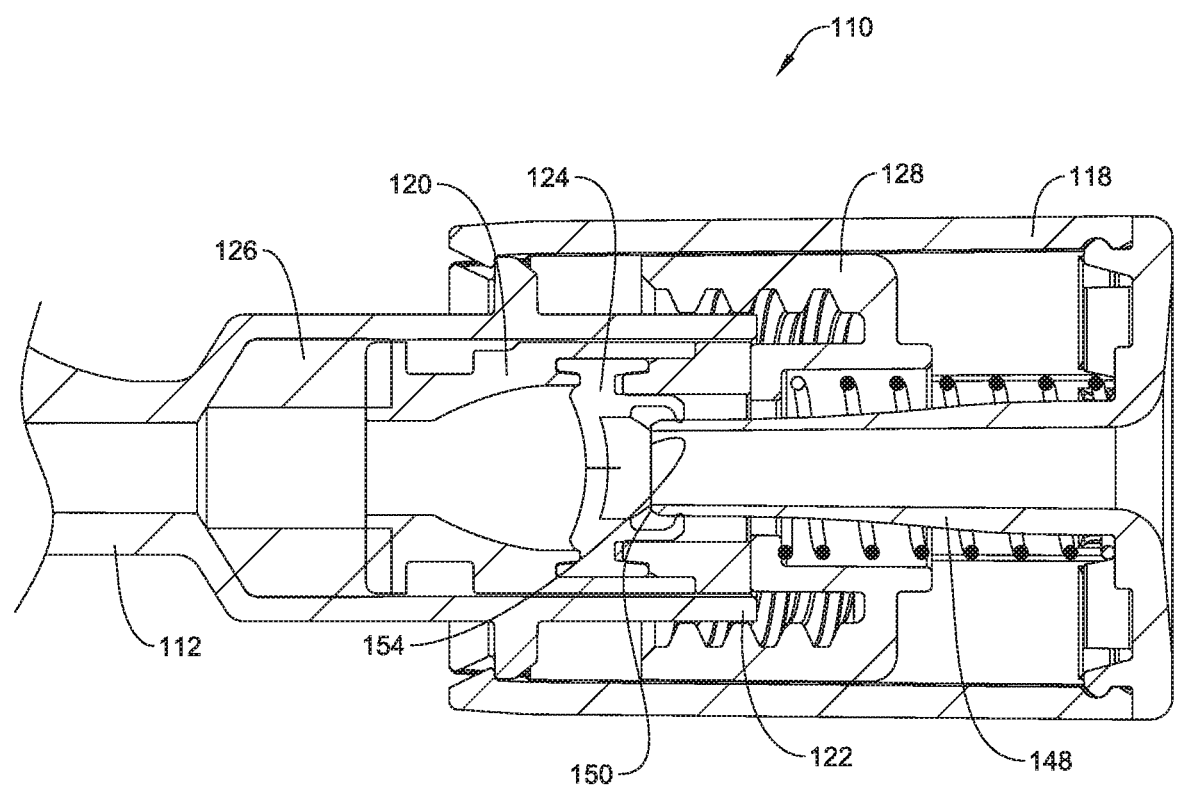
FIG. 7 is a cross-sectional view of a portion of an example hemostasis valve.

The plunger 118 may include an inner tubular region 148. The inner tubular region 148 may have a distal end 150. When the plunger 118 is positioned in the manner depicted in FIG. 6, the distal end 150 of the inner tubular region 148 is designed to be arranged such that a clearance distance 152 is defined between the distal end 150 of the inner tubular region 148 and a proximal end or surface 154 of the first seal member 124. In at least some instances, the clearance distance 152 is sufficiently small (e.g., on the order of about 0.1 to 5 mm or about 0.3 to 2 mm) so that when the first seal member 124 is exposed to elevated pressures, the proximal surface 154 of the first seal member 124 may slightly deform or shift into engagement with the distal end 150 of the inner tubular region 148 as shown in FIG. 7. When doing so, the distal end 150 of the inner tubular region 148 may provide additional structural support such that the first seal member 124 is able to substantially remain sealed at higher pressures. For example, the first seal member 124 may begin to deflect into engagement with the distal end 150 of the inner tubular region 14 when exposed to pressures of about 80-250 pounds per square inch (psi), or about 80-200 psi, or about 100-250 psi. Such a deflection can be understood as a partial deflection or modification, which is different from a modification where the first seal member 124 is opened or otherwise permits the flow of fluids therethrough. Because of the ability of the first seal member 124 to partially deflect into contact with the inner tubular region 148, the inner tubular region 148 may provide additional structural support to the first seal member 124 such that the first seal member 124 may be able to withstand pressures of about 100-500 psi or more, or about 170-400 psi or more, or about 250-270 psi or more.

It can be appreciated that a number of differing designs may be utilized for the hemostasis valve 110 that result in the desired clearance distance 152. For example, in some instances, the inner tubular region 148 of the plunger 118 may be sized so as to bring the inner tubular region 148 into the desired proximity of the first seal member 124. This may include the inner tubular region 148 extending distally beyond the distal end of the plunger 118, the inner tubular region 148 extending to the distal end of the plunger, the inner tubular region 148 extending to a position that is proximal of the distal end of the plunger 118. Likewise, the first seal member 124 may also be designed with structural features that provide the desired clearance distance 152. This may include the first seal member 124 having an increased thickness, a reduced thickness, etc. Furthermore, the cartridge 120 may also be designed with structural features that provide the desired clearance distance 152. For example, the cartridge 120 may be designed so that the position of the first seal member 124 therein may be shifted proximally or distally. Numerous other variations are contemplated.

EXAMPLES

The disclosure may be further clarified by reference to the following Examples, which serve to exemplify some embodiments, and not to limit the disclosure.

Example 1

A number of hemostasis valves similar to hemostasis valve 10 were manufactured without the plunger assembly attached. Tests were run to determine the amount of fluid pressure that could be applied until the first seal member began to leak fluid. It was determined that the average fluid pressure where leakage was observed for sample sterilized hemostasis valves at a time right after sterilization was 81.62 psi. It was also determined that the average fluid pressure where leakage was observed for sample sterilized hemostasis valves six months after sterilization was 79.98 psi.

Example 2

A number of hemostasis valves similar to hemostasis valve 110 were manufactured. Tests were run to determine the amount of fluid pressure that could be applied until the first seal member began to leak fluid. No leakage was observed at pressures of 300 psi, and leakage was not observed until pressures of 400 psi were applied.

Example 3

A number of hemostasis valves similar to hemostasis valve 110 were manufactured. Tests were run to determine the amount of fluid pressure that could be applied until the first seal member began to leak fluid under differing conditions. It was determined that the average fluid pressure where leakage was observed for sample sterilized hemostasis valves after a single "plunge" (e.g., which can be understood to be a single actuation of the plunger where the plunger is moved distally, rotated clockwise in order to close the second seal member, rotated counter-clockwise to open the second seal member, and the moved proximally) was 265.643 psi. It was also determined that after 50 "plunges", the average fluid pressure where leakage was observed was 257.467 psi.

The materials that can be used for the various components of the hemostasis valve 10 (and/or other hemostasis valves disclosed herein) and the various components thereof disclosed herein may include those commonly associated with medical devices. For simplicity purposes, the following discussion makes reference to the main body 12 and other components of the hemostasis valve 10. However, this is not intended to limit the devices and methods described herein, as the discussion may be applied to other hemostasis valves and/or components thereof disclosed herein.

The main body 12 and/or other components of the hemostasis valve 10 may be made from a metal, metal alloy, polymer (some examples of which are disclosed below), a metal-polymer composite, ceramics, combinations thereof, and the like, or other suitable material. Some examples of suitable polymers may include polytetrafluoroethylene (PTFE), ethylene tetrafluoroethylene (ETFE), fluorinated ethylene propylene (FEP), polyoxymethylene (POM, for example, DELRIN® available from DuPont), polyether block ester, polyurethane (for example, Polyurethane 85A), polypropylene (PP), polyvinylchloride (PVC), polyetherester (for example, ARNITEL® available from DSM Engineering Plastics), ether or ester based copolymers (for example, butylene/poly(alkylene ether) phthalate and/or other polyester elastomers such as HYTREL® available from DuPont), polyamide (for example, DURETHAN® available from Bayer or CRISTAMID® available from Elf Atochem), elastomeric polyamides, block polyamide/ethers, polyether block amide (PEBA, for example available under the trade name PEBAX®), ethylene vinyl acetate copolymers (EVA), silicones, polyethylene (PE), Marlex high-density polyethylene, Marlex low-density polyethylene, linear low density polyethylene (for example REXELL®), polyester, polybutylene terephthalate (PBT), polyethylene terephthalate (PET), polytrimethylene terephthalate, polyethylene naphthalate (PEN), polyetheretherketone (PEEK), polyimide (PI), polyetherimide (PEI), polyphenylene sulfide (PPS), polyphenylene oxide (PPO), poly paraphenylene terephthalamide (for example, KEVLAR®), polysulfone, nylon, nylon-12 (such as GRILAMID® available from EMS American Grilon), perfluoro(propyl vinyl ether) (PFA), ethylene vinyl alcohol, polyolefin, polystyrene, epoxy, polyvinylidene chloride (PVdC), poly(styrene-b-isobutylene-b-styrene) (for example, SIBS and/or SIBS 50A), polycarbonates, ionomers, biocompatible polymers, other suitable materials, or mixtures, combinations, copolymers thereof, polymer/metal composites, and the like. In some embodiments the sheath can be blended with a liquid crystal polymer (LCP). For example, the mixture can contain up to about 6 percent LCP.

Some examples of suitable metals and metal alloys include stainless steel, such as 304V, 304L, and 316LV stainless steel; mild steel; nickel-titanium alloy such as linear-elastic and/or super-elastic nitinol; other nickel alloys such as nickel-chromium-molybdenum alloys (e.g., UNS: N06625 such as INCONEL® 625, UNS: N06022 such as HASTELLOY® C-22®, UNS: N10276 such as HASTELLOY® C276®, other HASTELLOY® alloys, and the like), nickel-copper alloys (e.g., UNS: N04400 such as MONEL® 400, NICKELVAC® 400, NICORROS® 400, and the like), nickel-cobalt-chromium-molybdenum alloys (e.g., UNS: R30035 such as MP35-N® and the like), nickel-molybdenum alloys (e.g., UNS: N10665 such as HASTELLOY® ALLOY B2®), other nickel-chromium alloys, other nickel-molybdenum alloys, other nickel-cobalt alloys, other nickel-iron alloys, other nickel-copper alloys, other nickel-tungsten or tungsten alloys, and the like; cobalt-chromium alloys; cobalt-chromium-molybdenum alloys (e.g., UNS: R30003 such as ELGILOY®, PHYNOX®, and the like); platinum enriched stainless steel; titanium; combinations thereof; and the like; or any other suitable material.

The first seal member 124 (and/or other seal members disclosed herein) may be formed from a suitable material. For example, the seal member 124 may be formed from a silicone and/or silicone rubber material such as LSR6030, commercially available from Shenzhen SQUARE Silicone Co., Ltd. In some instances, the seal member 124 may be formed from an elastomeric material such as Q7-4720, Q7-4735, GUMSTOCK, or the like, which are commercially available from DOW CORNING.

It should be understood that this disclosure is, in many respects, only illustrative. Changes may be made in details, particularly in matters of shape, size, and arrangement of steps without exceeding the scope of the disclosure. This may include, to the extent that it is appropriate, the use of any of the features of one example embodiment being used in other embodiments. The invention's scope is, of course, defined in the language in which the appended claims are expressed.

What is claimed is:

1. A hemostasis valve, comprising:
a main body having a proximal end region;
a cartridge at least partially disposed within the proximal end region, the cartridge including a seal member;
wherein the seal member is designed to shift between an open configuration and a sealed configuration;
a plunger coupled to the proximal end region of the main body, the plunger having an inner tubular region having a distal end;
wherein the distal end of the inner tubular region is spaced a clearance distance from a proximal end of the seal member so that when the seal member is in the sealed configuration and exposed to pressures of 80-250 pounds per square inch, the seal member deflects into contact with the distal end of the inner tubular region and remains in the sealed configuration.

2. The hemostasis valve of claim 1, wherein the clearance distance has an axial dimension of 0.1 to 5 millimeters.

3. The hemostasis valve of claim 1, wherein the clearance distance has an axial dimension of 0.3 to 2 millimeters.

4. The hemostasis valve of claim 1, wherein the clearance distance is designed so that when the seal member is in the sealed configuration and exposed to pressures of 100-250 pounds per square inch, the seal member deflects into contact with the distal end of the inner tubular region and remains in the sealed configuration.

5. The hemostasis valve of claim 1, wherein the clearance distance is designed so that when the seal member is in the sealed configuration and exposed to pressures of 80-200 pounds per square inch, the seal member deflects into contact with the distal end of the inner tubular region and remains in the sealed configuration.

6. The hemostasis valve of claim 1, wherein the proximal end region of the main body includes a retaining protrusion.

7. The hemostasis valve of claim 6, wherein the plunger has a distal retaining flange designed to engage the retaining protrusion.

8. The hemostasis valve of claim 1, wherein a spring member is disposed within the plunger and engaged with a proximal end of the plunger.

9. The hemostasis valve of claim 1, further comprising a nut threadably engaged with one or more threads along the proximal end region of the main body.

10. The hemostasis valve of claim 1, wherein the inner tubular region has a wall thickness that varies along the length thereof.

11. The hemostasis valve of claim 1, wherein the inner tubular region has an inner diameter that varies along the length thereof.

12. A hemostasis valve, comprising:
a main body having a proximal end region;
a cartridge at least partially disposed within the proximal end region, the cartridge including a seal member;
wherein the seal member is designed to shift between an open configuration and a sealed configuration;
a plunger coupled to the proximal end region of the main body, the plunger having an inner tubular region having a distal end;
wherein the seal member and the plunger are arranged so that there is a clearance distance between a proximal face of the seal member and the distal end of the inner tubular region such that when the seal member is in the sealed configuration and exposed to pressures of 80-250 pounds per square inch, the proximal face of the seal member deflects into contact with the distal end of the inner tubular region and remains in the sealed configuration.

13. The hemostasis valve of claim 12, wherein the clearance distance has an axial dimension of 0.1 to 5 millimeters.

14. The hemostasis valve of claim 12, wherein the clearance distance has an axial dimension of 0.3 to 2 millimeters.

15. The hemostasis valve of claim 12, wherein the clearance distance is designed so that when the seal member is in the sealed configuration and exposed to pressures of 100-250 pounds per square inch, the seal member deflects into contact with the distal end of the inner tubular region and remains in the sealed configuration.

16. The hemostasis valve of claim 12, wherein the clearance distance is designed so that when the seal member is in the sealed configuration and exposed to pressures of 80-200 pounds per square inch, the seal member deflects into contact with the distal end of the inner tubular region and remains in the sealed configuration.

17. The hemostasis valve of claim 12, wherein the proximal end region of the main body includes a retaining protrusion and wherein the plunger has a distal retaining flange designed to engage the retaining protrusion.

18. The hemostasis valve of claim 12, further comprising a nut threadably engaged with one or more threads along the proximal end region of the main body.

19. A hemostasis valve, comprising:
a main body having a threaded proximal end region;
a nut threadably engaged with the threaded proximal end region;
a cartridge at least partially disposed within the threaded proximal end region, the cartridge including a seal member;
wherein the seal member is designed to shift between an open configuration and a sealed configuration;
a plunger coupled to the threaded proximal end region of the main body, the plunger having an inner tubular region having a distal end;
wherein the seal member and the plunger are arranged so that there is a clearance distance between a proximal face of the seal member and the distal end of the inner tubular region such that when the seal member is in the sealed configuration and exposed to pressures of 80-250 pounds per square inch, the proximal face of the seal member deflects into contact with the distal end of the inner tubular region and remains in the sealed configuration.

20. The hemostasis valve of claim 19, wherein the clearance distance has an axial dimension of 0.3 to 2 millimeters and wherein the clearance distance is designed so that when the seal member is in the sealed configuration and exposed to pressures of 80-200 pounds per square inch, the seal member deflects into contact with the distal end of the inner tubular region and remains in the sealed configuration.

* * * * *